United States Patent [19]

Suga

[11] Patent Number: 5,615,685
[45] Date of Patent: Apr. 1, 1997

[54] PERSONAL PHYSICAL FITNESS MEASURING APPARATUS

[75] Inventor: Fusao Suga, Ome, Japan

[73] Assignee: Casio Computer Co., Ltd., Tokyo, Japan

[21] Appl. No.: 446,411

[22] Filed: May 22, 1995

[30] Foreign Application Priority Data

May 30, 1994 [JP] Japan .................................. 6-116182

[51] Int. Cl.⁶ .................................................. A61B 5/02
[52] U.S. Cl. ......................... 128/670; 128/668; 128/669; 128/687; 128/706; 128/707
[58] Field of Search .................... 128/668–670, 128/687–690, 706, 707

[56] References Cited

U.S. PATENT DOCUMENTS

| | | | |
|---|---|---|---|
| 3,675,640 | 7/1972 | Gatts . | |
| 4,202,350 | 5/1980 | Walton | 128/690 |
| 4,312,358 | 1/1982 | Barney . | |
| 4,343,315 | 8/1982 | O'Leary | 128/689 |
| 4,566,461 | 1/1986 | Lubell et al. | 128/689 |
| 4,807,639 | 2/1989 | Shimizu et al. . | |
| 5,301,154 | 4/1994 | Suga . | |

FOREIGN PATENT DOCUMENTS

| | | |
|---|---|---|
| 0117330 | 9/1984 | European Pat. Off. . |
| 0172747 | 2/1986 | European Pat. Off. . |
| 0556702A2 | 8/1993 | European Pat. Off. . |
| 5056702A2 | 8/1993 | European Pat. Off. . |

*Primary Examiner*—Angela D. Sykes
*Assistant Examiner*—Stephen Huang
*Attorney, Agent, or Firm*—Frishauf, Holtz, Goodman, Langer & Chick

[57] ABSTRACT

A control unit of a measuring apparatus controls a sound driving circuit to make a sounding unit generate pitch sounds at a predetermined pace for three minutes. After generation of the pitch sounds for three minutes, a heart rate sensor measures a heart rate of an exerciser who has executed an exercise in synchronism with the generated pitch sounds, and the measured heart rate is stored in RAM. Further, the control unit controls the sounding unit to generate pitch sounds at a different pace for another three minutes, and a heart rate of the exerciser is measured and stored similarly. Based on the measured heart rates and personal data such as an age of the exerciser input through a key input unit, a level of objective physical strength of the exerciser is calculated and displayed on a display device. In other words, physical strength of the exerciser is objectively evaluated based on physical data such as a heart rate that varies when the exerciser performs the exercise.

8 Claims, 6 Drawing Sheets

PERSONAL PHYSICAL FITNESS MEASURING APPARATUS

BACKGROUND OF THE INVENTION

1. Field of the Invention

The present invention relates to a measuring apparatus which is used by an exerciser to measure his or her physical data such as heart rates and to obtain objective physical-strength evaluation data based on the measured physical data.

2. Description of the Prior Art

Apparatus are known which measures heart rates of an exerciser to advise him (or her) how much his (or her) physical strength has been improved. Further, apparatus are known which advises as to the difficulty of exercise performed by the exerciser. For instance, U.S. Pat. No. 4,807,639 discloses a device which measures a heart rate of an exerciser immediately after the exerciser has performed an exercise, and indicates in percent a ratio of the measured heart rate to a predetermined heart rate. In the case where the exerciser performs a similar exercise, his heart rate will go down as his physical strength is improved. Therefore, decrease of the above ratio expressed in percent shows that his physical strength has been improved.

Further, in published European Patent Application No. 0556702 is disclosed a device that calculates difficulty of exercise performed by the exerciser from a measured heart rate and age data of the exerciser. The device measures a heart rate of the exerciser, calculates a ratio of the measured heart rate to a reference heart rate that is equivalent to a difference between 220 and an age of the exerciser, and indicates the calculated ratio in percent as hardness of exercise performed by the exerciser.

When the exerciser performs a similar exercise, measured heart rate decreases as his physical strength is improved. The device shows that difficulty of exercise expressed in the calculated ratio in percent decreases, and his physical strength has been improved.

The exerciser can learn time-sequentially whether his physical strength has been improved or not with the use of these devices. In these devices, however, the exerciser can not compare his physical strength with a reference physical strength. In other words, if the exerciser is, for example, 20 years old, the exerciser can not learn with the use of these devices, whether his measured physical strength is higher than the reference physical strength of a man of 20 years old.

SUMMARY OF THE INVENTION

The present invention has been made to overcome the above mentioned inconvenience, and has an object to provide a measuring apparatus that is capable of measuring physical data of an exerciser, which changes due to exercise performed by the exerciser, to objectively evaluate physical strength of the exerciser.

According to one aspect of the invention, there is provided a measuring apparatus which comprises:

heart-rate measuring means for measuring heart rates of an exerciser to obtain heart rate data when the exerciser performs a predetermined exercise several times under different conditions, respectively;

heart-rate data storing means for storing heart rate data obtained by said heart-rate measuring means;

physical-strength evaluation calculating means for calculating physical-strength evaluation data based on plural heart rate data stored in said heart-rate data storing means, wherein said physical-strength evaluation calculating means includes judging means for judging to which one of plural predetermined physical-strength evaluation data the calculated physical-strength evaluation data corresponds; and output means for outputting the physical-strength evaluation data calculated by said physical-strength evaluation calculating means.

With the use of the measuring apparatus with the above structure, physical strength of an exerciser can be evaluated from heart rate data of the exerciser that are measured when an exerciser performs a predetermined exercise several times under different conditions.

It would be apparent to those skilled in the art from the following description of preferred embodiments that the present invention may be modified in various manners and may be applicable to other apparatus.

BRIEF DESCRIPTION OF THE DRAWINGS

Other objects and structures of the present invention will be more fully understood from the description, when taken in conjunction with the accompanying drawings, in which.

DETAILED DESCRIPTION OF PREFERRED EMBODIMENTS

Now, a preferred embodiment of the present invention will be described in detail with reference to the accompanying drawings.

Figure 1:
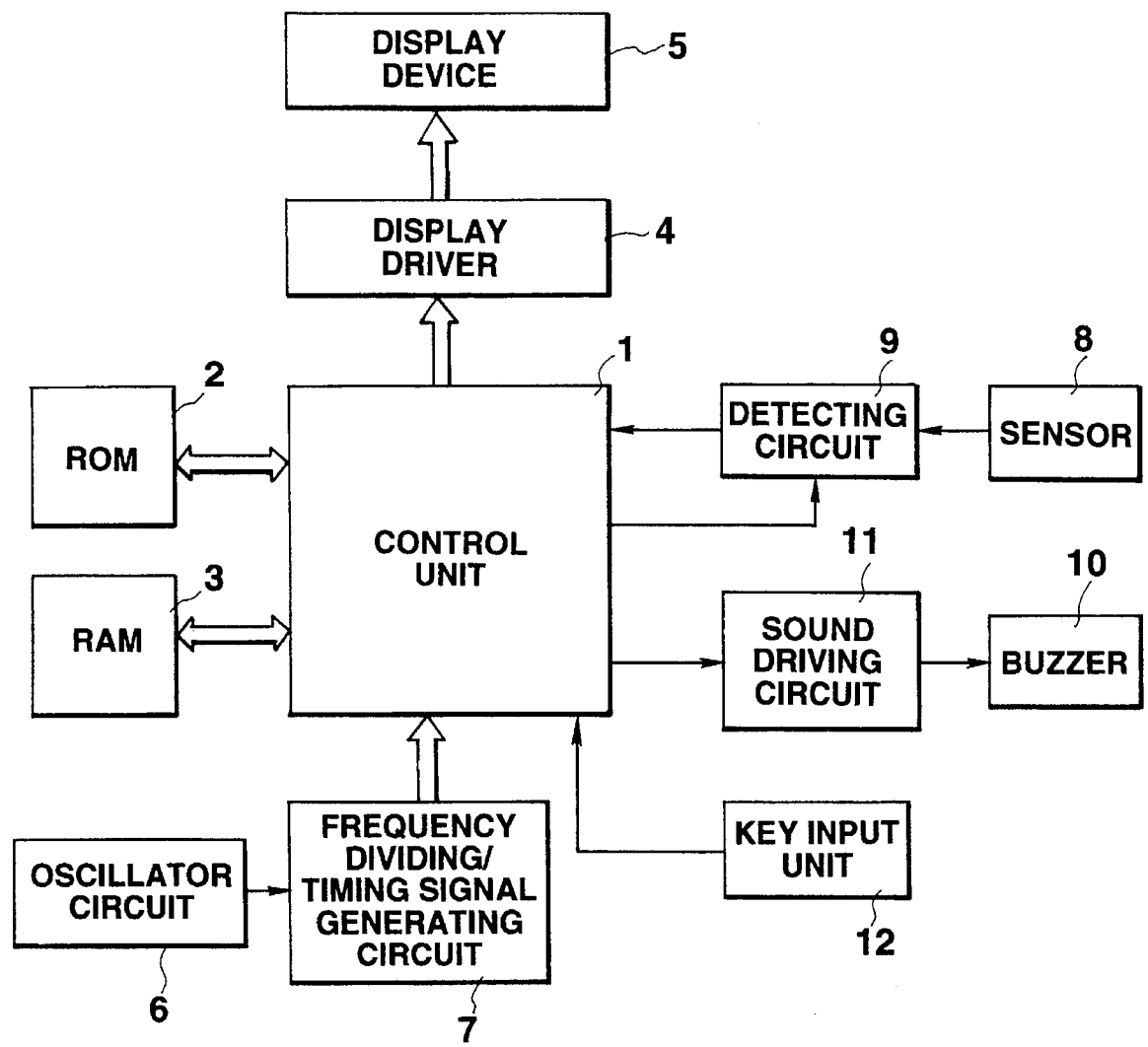
FIG. 1 is a circuit diagram of an embodiment of a wrist watch according to the present invention.

FIG. 1 is a circuit diagram of an electronic apparatus such as an electronic wrist watch, which is used for evaluating physical strength of a user or an exerciser.

In FIG. 1, a control unit 1 including a central processing unit (CPU) executes a time counting program for counting a current time and various process programs for evaluating physical strength of the exerciser in accordance with a microprogram stored in a read only memory (ROM) 2. As will be described below, the ROM 2 stores various data for evaluating physical strength of the exerciser in addition to the microprogram.

Data memory unit 3, i.e., a random access memory (RAM) 3, stores various data, as will be described in detail later. Various data stored in the RAM 3 and data which are read out from the ROM 2 based on the various data stored in the RAM 3 are displayed through a display driver 4 on a display device 5 such as a dot-matrix liquid crystal display device.

An oscillator circuit 6 including, for example, a crystal oscillator circuit generates an oscillating signal of a predetermined frequency, and supplies the oscillating signal to a frequency dividing/timing signal generating circuit 7. The frequency dividing/timing signal generating circuit 7 divides the oscillating signal supplied from the oscillator circuit 6 to obtain a system clock signal for controlling a whole circuit, various timing signals and a time counting signal for counting a time. These signals are supplied to the control unit 1.

A pulse sensor 8 is comprised of a light emitting diode and a photo transistor, and is used to count a heart rate of the user or the exerciser. The pulse sensor 8 receives a signal from a pulse detecting circuit 9 to detect a heart rate, and supplies the detected signal to the pulse detecting circuit 9. Receiving an operation instruction signal from the control unit 1, the pulse detecting circuit 9 makes the pulse sensor 8 operate to calculate pulse data (a pulse rate) per unit time, for instance, a minute, based on time intervals of pulses. The calculated pulse data is supplied to the control unit 1.

A sounding unit 10, which includes, for example, a buzzer, generates a pace sound based on a sound signal supplied from a sound driving circuit 11, as will be described later. Upon receipt of a sound signal of a pace sound having predetermined periods from the control unit 1, the sound driving circuit 11 supplies a sound driving signal to the sounding unit 10.

A key input unit 12 comprises plural push-button switches K1–K4, and supplies the control unit 1 with a switch signal of a depressed push-button switch.

Figure 2:
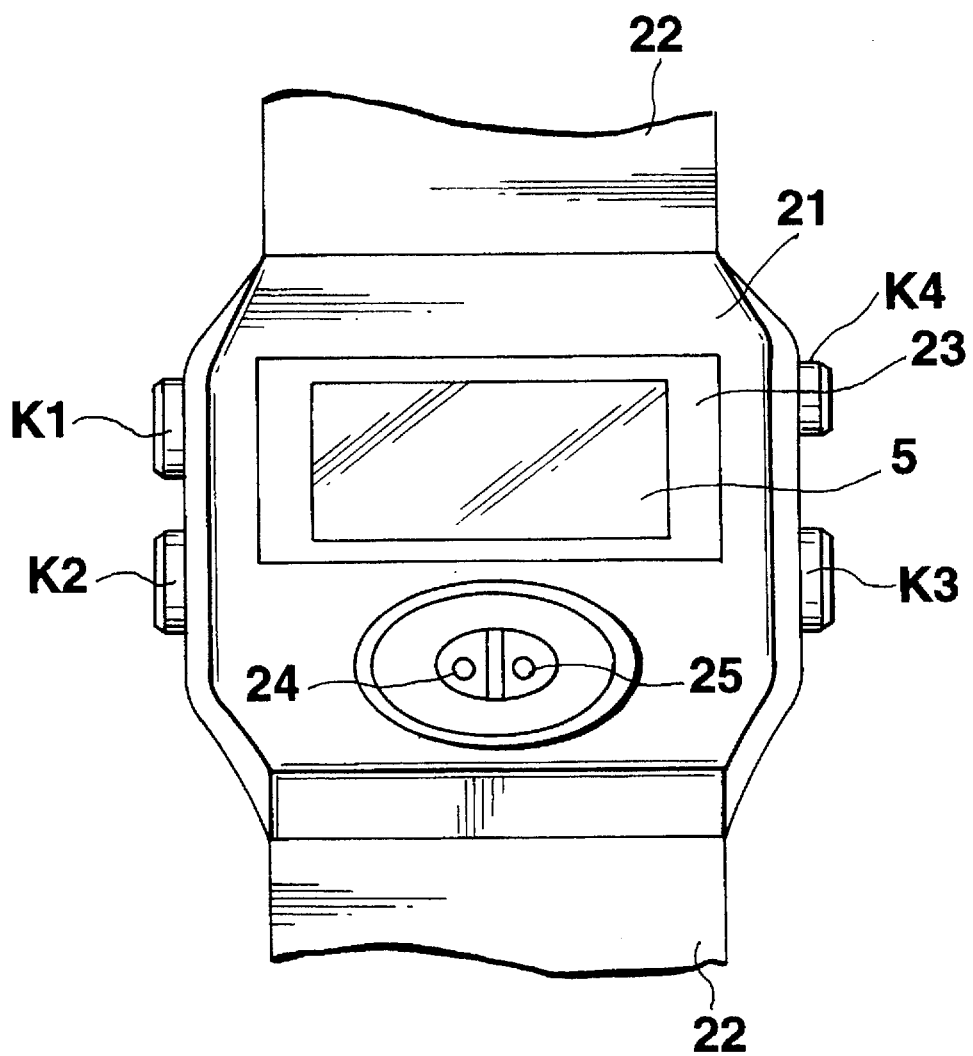
FIG. 2 is a front external view of the wrist watch.

FIG. 2 is a plan view showing a front face of an electronic wrist watch, in which the above circuits are incorporated. Watch straps 22, 22 are connected to two sides of a watch casing 21 (i.e., to a top portion and a bottom portion of the watch casing 21 as viewed in FIG. 2). The watch casing 21 is provided with a watch glass 23 at an approximately center portion thereof, and the display device 5 is mounted in the watch casing 21 just behind the watch glass 23. At a lower portion on the front surface of the watch casing 21, there are provided a light emitting diode 24 and a photo transistor 25. A user can take his (or her) a heart rate or pulses with his finger put on the watch casing so as to cover the light emitting diode 24 and the photo transistor 25.

The push-button switches K1–K4 are installed in both side walls of the watch casing 21. Though not shown in FIG. 2, the sounding unit 10 comprises a rear cover of the watch casing 21 and a piezoelectric element (not shown). The piezoelectric element is affixed on an interior surface of the rear cover of the watch casing 21 and is driven by a signal supplied from the alarm driving circuit 11.

Figure 3:
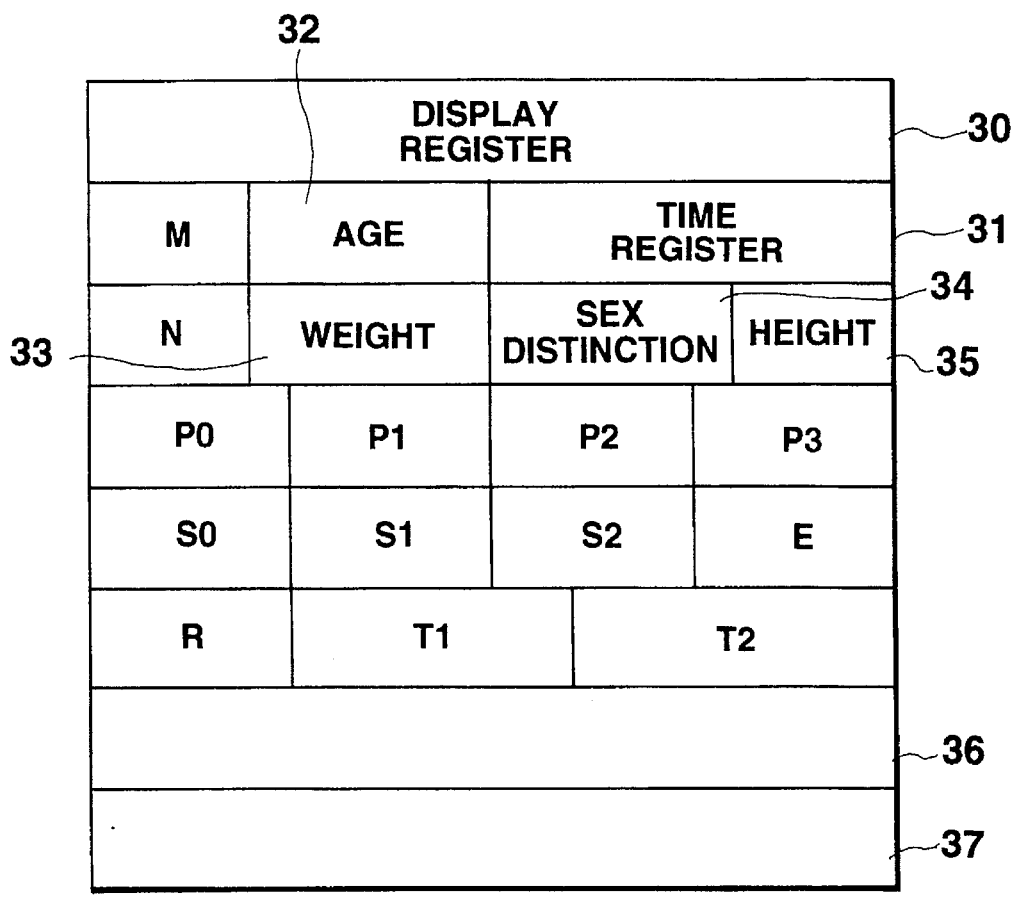
FIG. 3 is a view showing a detailed structure of RAM shown in FIG. 2.

FIG. 3 is a view showing a structure (memory areas) of the RAM 3. A display register 30 stores data to be displayed on the display unit 5. A register M is a mode register for storing mode data (mode indications) representing display modes. A value of the mode register M, "0" (i.e., a mode value "M=0"), represents a time display mode, in which a current time is displayed on the display device 5. A mode value "M=1" represents a measurement mode, in which a measurement is made for evaluating physical strength of the user and resultant data are displayed on the display device 5. A mode value "M=2" represents a data setting mode. In the data setting mode, personal data such as age data, weight data, sex distinction of a user are set, which are necessary for evaluating physical strength of the person, and further height data of a footstool is set, which is used by the user to perform a footstool on/down exercise. That is, to perform the footstool on/down exercise, the user repeatedly steps up on and down from the footstool for a predetermined period of time.

A register 31 stores current time data including year data, date data and time data. A number register N stores number data which represents how many times the user has repeatedly performed the footstool up/down exercise.

Registers 32, 33, 34 and 35 store age data, weight data, sex distinction data of the user and footstool height data, respectively. A register P0 stores pulse data (sometimes, referred to as heart rate data) of the user measured before the user executes the footstool up/down exercise. A register P1 stores heart rate data of the user measured immediately after the user has executed the footstool up/down exercise for the first time. A register P2 stores heart rate data of the user measured after the user has executed the footstool up/down exercise for the second time. A register P3 stores heart rate data of the user measured after the user has executed the footstool up/down exercise for the third time.

Registers S0, S1 and S2 store pace sound data which represent the number of sounds to be generated in a predetermined period of time, for instance, in a minute. The pace sound data is decided for the footstool up/down exercise, based on age data stored in the age register 32. The register S0 stores pace sound data for the first footstool up/down exercise. The register S1 stores pace sound data for the second footstool up/down exercise. The registers 2 stores pace sound data for the third footstool up/down exercise.

A register E stores error data representative of a type of an error which occurs during measurement. A register R stores work load data and physical-strength evaluation data which are calculated from the above data.

Registers T1 and T2 are timer registers. The timer register T1 is for counting a time duration of 3 minutes, and the timer register T2 is for counting a time duration of 20 seconds. Registers 36 and 37 are used as a work area for performing a calculating operation.

Now, operation of the wrist watch with the above structure will be described.

Figure 4:
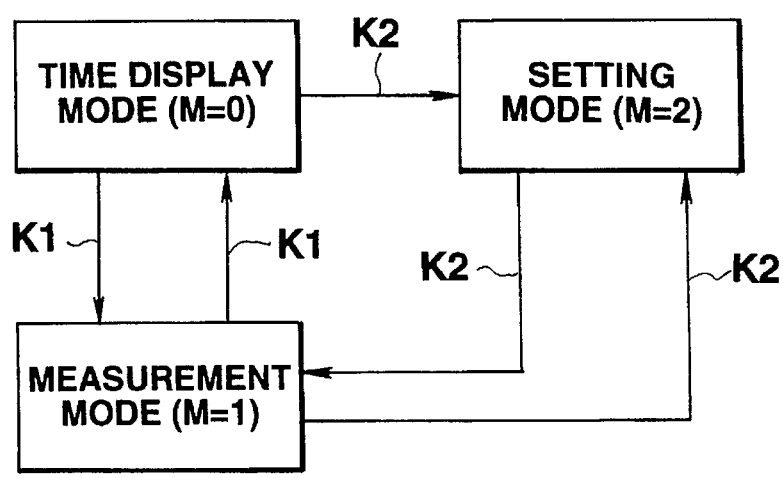
FIG. 4 is a view showing transit indications displayed on a display unit of FIG. 2.

FIG. 4 is a view showing transitive mode data (mode indications) displayed on the display device 5, which mode data are changed by operation of the push-button switches K1 and K2. When the mode register M is set to "0", i.e., "M=0", the time display mode is set, in which the current time data including a year, date and a time is sent to the display register 30 and is displayed on the display device 5. When the push-button switch K1 is depressed in the time display mode, the mode register M is incremented by "+1" to be set to "1", whereby the time display mode is changed to the measurement mode. An operation that will be performed in the measurement mode and indications displayed on the display device 5 will be described later.

When the push-button switch K2 is operated in the time display mode, the value of the mode register M is added by "+2" to be set to "2" ("M=2"), whereby the setting mode is set. When the push-button switch K2 is operated in the measurement mode, the value of the mode register M is added by "+1" and is set to "2" ("M=2"), whereby the setting mode is set. In the setting mode, age data, weight data, sex data and footstool height data in the registers 32, 33, 34 and 35 are displayed on the display device 5, wherein an initial setting or renewal of contents of the registers are allowed. Contents of the registers to be initialized or renewed are designated by operation of the push-button switch K3, and the designated content is successively incremented by "+1" every operation of the push-button switch K4, wherein contents of the registers are changed and set.

When the push-button switch K2 is operated in the setting mode, the value of the mode register M is subtracted by "1"

and is set to "1" ("M=1"), whereby the setting mode is changed to the measurement mode.

Figure 5:
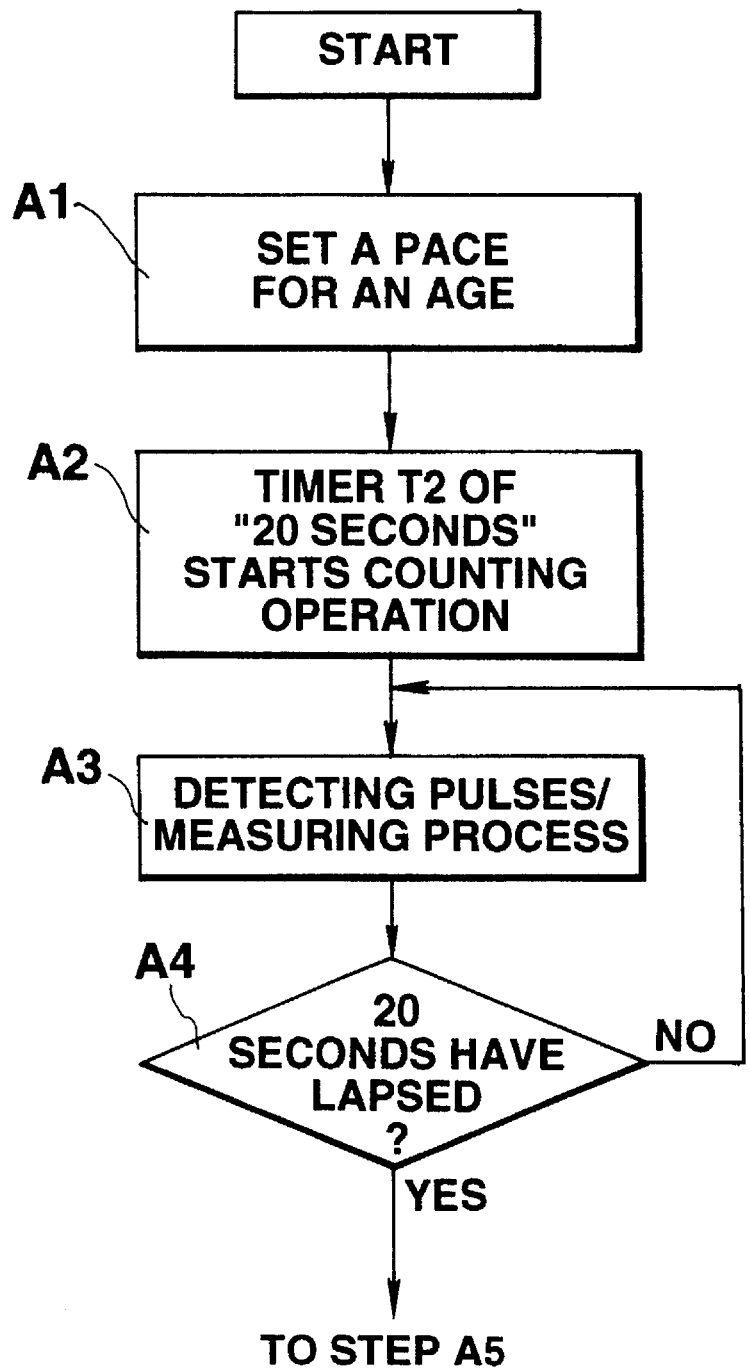
FIG. 5 is a flowchart (first half) of operation of the embodiment of FIG. 1.
Figure 6:
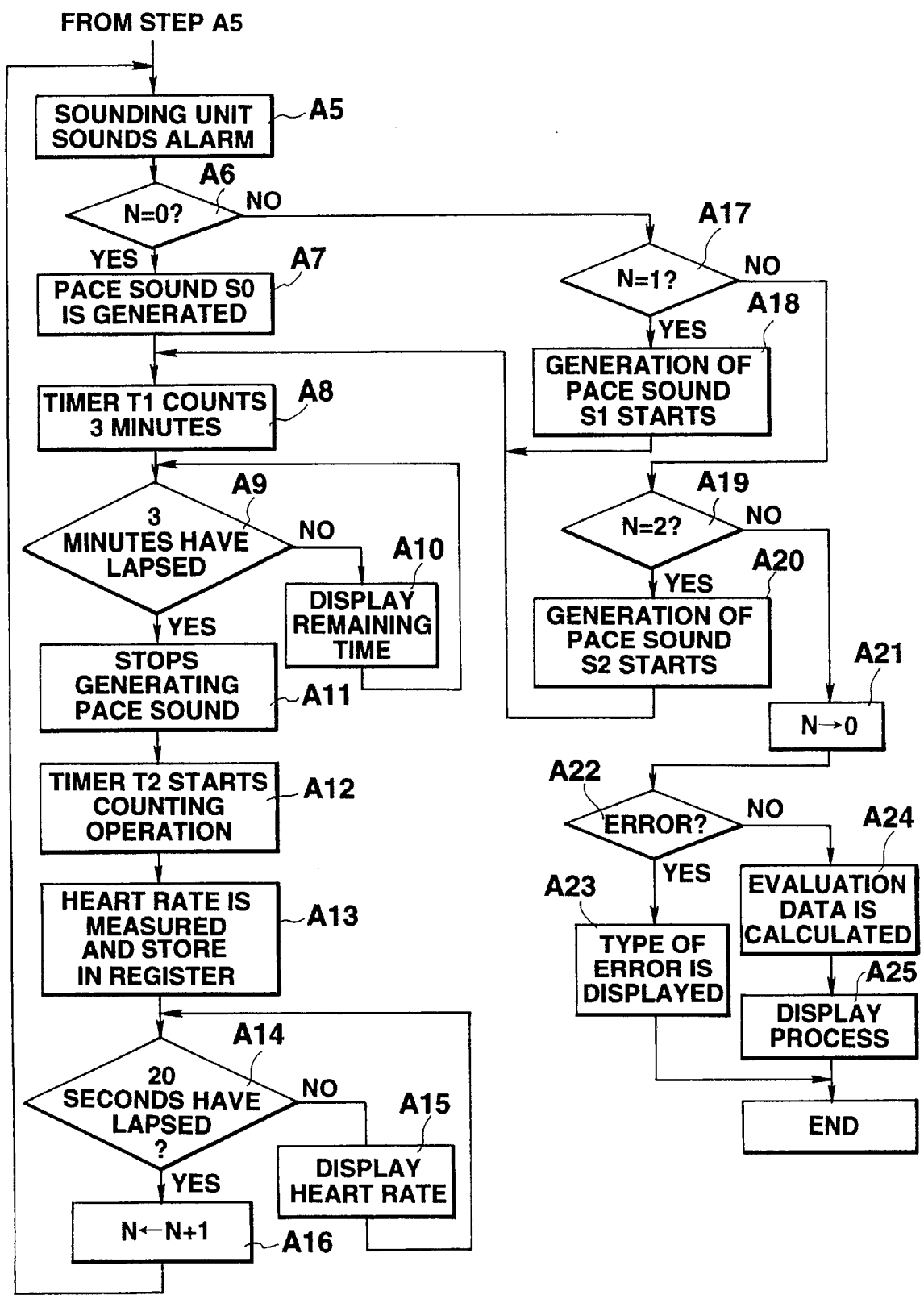
FIG. 6 is a flowchart (second half) of operation of the embodiment of FIG. 1.

FIGS. 5 and 6 are flowcharts of operation to be performed in the measurement mode. In the present embodiment, the user (an exerciser) performs footstool up/down exercises at different paces for three minutes for three times, and he (or she) takes rests between the footstool up/down exercises for 20 seconds. Every after performing each exercise, a pulse rate of the exerciser is measured to obtain evaluation data for evaluating his (or her) physical strength. In the ROM 2 are stored pace data for respective ages, operation data, comparison data (work load data). The pace data, the operation data and the work amount data will be described later. The comparison data is reference data of a reference exerciser of the same sex and of the same age as the exerciser, which reference data is to be compared with obtained physical strength data to objectively evaluate physical strength of the exerciser.

When the time display mode is switched to the measurement mode, or when the setting mode is changed to the measurement mode, operation starts in accordance with the flowchart of FIG. 5.

At step A1 in the flowchart of FIG. 5, three pace data for the footstool up/down exercise based on the age data stored in the age register 32 are stored in the registers S0, S1 and S2, respectively. More specifically, in the ROM 2 are stored pace data per minute with respect to three age ranges as shown below. These pace data are stored in the registers S0, S1 and S2 respectively at step A1.

| | Pace data | | |
|---|---|---|---|
| registers | S0 | S1 | S2 |
| ages 13–29 | 90 | 110 | 130 |
| ages 30–39 | 80 | 100 | 120 |
| ages 40–79 | 70 | 90 | 110 |

For example, in the case that the age of the exerciser falls in a range of 13 to 29, a pace of "90/minute" for the first exercise is stored in the register S0. Further, paces of "110/minute" and "130/minute" for the second and the third exercise are stored in the registers S1 and S2, respectively.

As will be clear from the above table, the pace (110/minute) for the second exercise is higher than the pace (90/minute) for the first exercise, and the pace (130/minute) for the third exercise is higher than the pace for the second exercise, which means that the second exercise is harder than the first exercise and the third exercise is harder than the second exercise.

At step A2, the timer register T2 of "20 seconds" is cleared, and the timer register T2 is caused to start the time counting operation again. At step A3, the pulse detecting circuit 9 judges whether a pulse signal (or a heart rate signal) is generated. Detecting the pulse signal, the pulse detecting circuit 9 calculates the number of pulses per minute (a heart rate) from the detected pulse signal, stores the calculated heart rate in the register P0, and displays same on the display device 5. Then, putting his finger on the light emitting diode 24 and the photo transistor 25, the exerciser can measure and display his heart rate before performing the exercise. Therefore, independently of exercise for evaluating physical strength, the exerciser can measure and display his heart rate on the display device 5 any time he likes, by putting his finger on the diode 24 and the transistor 25.

After the heart rate has been measured at step A3, or when the pulse signal was not detected, operation goes to step A4, where it is judged whether the timer register T2 has counted 20 seconds. When NO (When it is determined that 20 seconds have not yet lapsed), processes at steps A3 and A4 are repeatedly executed.

When it is determined at step A3 that 20 seconds have lapsed, operation advances from step A3 to step A5 of FIG. 6. At step A5, the sounding unit 10 sounds an alarm through the sound driving circuit 11, to tell the exerciser to start the footstool up/down exercise again. At step A6, it is judged whether the number register N has been set to "0" (i.e., whether "N=0" is true). Since "N=0" is true, operation goes to step A8.

At step A7, the sounding unit 10 starts generating pace sounds at a pace determined based on the pace data of the first exercise stored in the register S0. The sounds generated by sounding unit 10 at step A7 are different (in frequency and sound level) from the alarm sounded at step A5 for starting the exercise. As will be described later, the sounding unit 10 keeps generating the pace sounds for three minutes until a pace-sound stop process stops the sounding unit 10 from generating the pace sounds at step A11.

At step A8, the timer register T1 of "three minutes" is cleared and starts a counting operation again. At the following step A9, it is judged whether the timer register T1 has counted three minutes, i.e., whether three minutes have lapsed after the timer register T1 started the counting operation. When NO (When it is determined that three minutes have not yet lapsed), the remaining time is displayed on the display device 5 at step A10 before three minutes lapse. Thereafter, processes at steps A9 and A10 are repeatedly executed.

When three minutes have lapsed, the pace-sound stop process is executed at step A11 to stop the sounding unit 10 from sounding the pace sounds. Therefore, at the alarm sounded at A5, the exerciser starts the first exercise, and keeps stepping up and down on the footstool for three minutes in synchronism with the pace sounds generated based on the pace data stored in the register S0. Then, after three minutes, the exerciser finishes the first exercise.

When the pace sounds stop at step A11, the timer register T2 of "20 seconds" is cleared at step A12 and starts a time counting operation again. At the following step A13, pulse is detected, and detected pulse data (heart rate data) is stored in any one of the registers P1, P2 and P3. The heart rate data is obtained by dividing a value "60" by a measured time interval between two adjacent pulses.

In this case, the register in which heart rate data is to be stored is decided by a value of the N register. When N="0", heart rate data obtained immediately after the first exercise is stored in the register P1. When N="1", heart rate data measured after the second exercise is stored in the register P2. When N="2", heart rate data measured after the third exercise is stored in the register P3. Since N="0" is true at this time, the obtained heart rate data is stored in the register P1.

When a heart rate of the exerciser is measured and stored in the register P1 at step A13, it is judged at step A14 whether the timer register T2 has counted 20 seconds, and the obtained heart rate data is displayed on the display device 5 at step A15 till 20 seconds lapse. The exerciser can take a rest during a time of these 20 seconds.

After 20 seconds, operation goes to step A16, where the register N is incremented by "+1", and returns to step A5. At step A5, the sounding unit 10 sounds an alarm to tell the exerciser to start the footstool up/down exercise again. At step A6, it is judged whether the number register N has been set to "0" (i.e., whether "N=0" is true). Since "N=0" is not true, operation goes to step A17, where the register N is incremented by "+1". Then, since the register N has been set to "1" (now, "N=1" is true), operation goes to step A17.

It is determined at step A17 that "N=1" is true, and operation goes to step A18, where generation of the pace sound starts in a similar manner described at step A7. At step A18, the pace sound is generated based on the pace data stored in the register S1, but, as described above, at step A7, the pace sound is generated based on the pace data stored in the register S0.

The generation of the pace sound starts at step A18, and then the operation goes to step A8. Thereafter, processes at steps A9 to A14 are performed. More specifically, the pace sound is generated for three minutes and then it comes a rest time of 20 seconds. During the rest time, since "N=1" is true, heart rate data measured at step A13 is stored in the register P2 as heart rate data for the second exercise.

After 20 seconds, the value of the register N is incremented by "+1" at step A16, whereby the register N is set to "2", and then operation returns to step A5, where the alarm is sounded to tell the exerciser to start the footstool up/down exercise. It is judged at step A6, whether "N=0" is true, and, as "N=2" is true at this time, operation goes to step A17 and further to step A19. At step A19, it is determined that "N=2" is true, and operation goes to step A20.

Generation of the pace sound based on the pace data stored in the register S2, i.e., based on pace data for the third exercise starts at step A20.

When the generation of the pace sound has started at step A20, operation goes to step A8, and thereafter processes at steps A9 to A15 are performed. More specifically, the pace sound is generated for three minutes and then it comes a rest time of 20 seconds. During the rest time, since "N=2" is true, heart rate data measured at step A13 is stored in the register P2 as heart rate data for the third exercise.

After 20 seconds, the value of the register N is incremented by "+1" at step A16, wherein the register N is set to "3", and then operation returns to step A5, where the alarm is sounded again to tell the exerciser to start the footstool up/down exercise. But since the exerciser has performed footstool up/down exercise three times, the pace sound is not generated and the alarm serves to tell that the measurement has been finished, as will be described later. Since "N=3" is true after step A5, operation goes to step A21 through steps A6, A17 and A19. At step A21, the register N is set to "0" ("N=0"). Then, at step A22 it is judged if measured heart rate data includes an error.

At step A22, four types of errors are detected. It is judged whether a first type of error has occurred. That is, it is determined that the first type error has occurred, when weight data, sex distinction data, height data of the footstool have not been stored in the pertinent registers 33, 34 and 35, respectively, or when extremely abnormal data has been stored in any one of the registers 33, 34 and 35.

Further, it is determined that the second type of error has occurred, when heart rate data have not been stored in the registers P0, P1, P2 and P3, i.e., when a normal measurement of a heart rate has not been made. It is determined that the third error has occurred, when heart rate data stored in the registers are extremely high or low. It is determined that the fourth error has occurred, when relationship between successively measured heart rate data is abnormal. In other words, the heart rate data stored in the register P0 was measured before the exerciser performed the exercise, and should be lowest among the heart rate data stored in the registers P0–P3. The heart rate data stored in the registers P1, P2 and P3 were measured after the exerciser performed the exercise. As described before, the heart rate data stored in the register P1 was measured after the exerciser performed the first exercise, the heart rate data stored in the register P2 was measured after the second exercise, and the heart rate data stored in the register P3 was measured after the third exercise. The exerciser takes the second exercise at a higher pace than a pace for the first exercise, and further the exerciser takes the third exercise at a higher pace than a pace for the second exercise. Therefore, the second exercise is harder than the first exercise, and the heart rate data of the register P2 measured after the exerciser performed the second exercise is expected to be higher than the heart rate data of the register P1 measured after the first exercise. Similarly, the third exercise is harder than the second exercise, and the heart rate data of the register P3 measured after the exerciser performed the third exercise is expected to be higher than the heart rate data of the register P2 measured after the second exercise. If these pulse data of the registers P1–P3 do not show the above relationship, it is determined that the fourth error has occurred.

Data representative of the error type, which data is detected at step A22, is stored in the register E. At step A23, data representative of the error type is displayed on the display unit. For instance, an indication of "an error has occurred during the second measurement" is displayed. Then, a process for returning the operation mode to the display mode is performed after a predetermined time, for instance, one minute has lapsed. In other words, a value of the register M is set to "0".

In case the second error has occurred, i.e., that heart rate data has not been stored in any of the registers P1–P3, the value of the register N is set to a corresponding value after display of the above indication, whereby the process at step A5 and processes thereafter are executed again. That is, the exerciser performs the exercise for which heart rate data was not obtained and further performs the exercise following the former exercise.

When no error has occurred at step A22, the operation goes to step A24, where evaluation data for evaluating physical strength is calculated. Work load is compared with average work load decided for the age and the sex distinction of the exerciser to evaluate the physical strength of the exerciser, work load which is achieved by the exerciser under evaluation when the exerciser performs exercise at a pace of a heart rate corresponding to 65% of the maximum pulse rate decided for the age of the exerciser.

Figure 7:
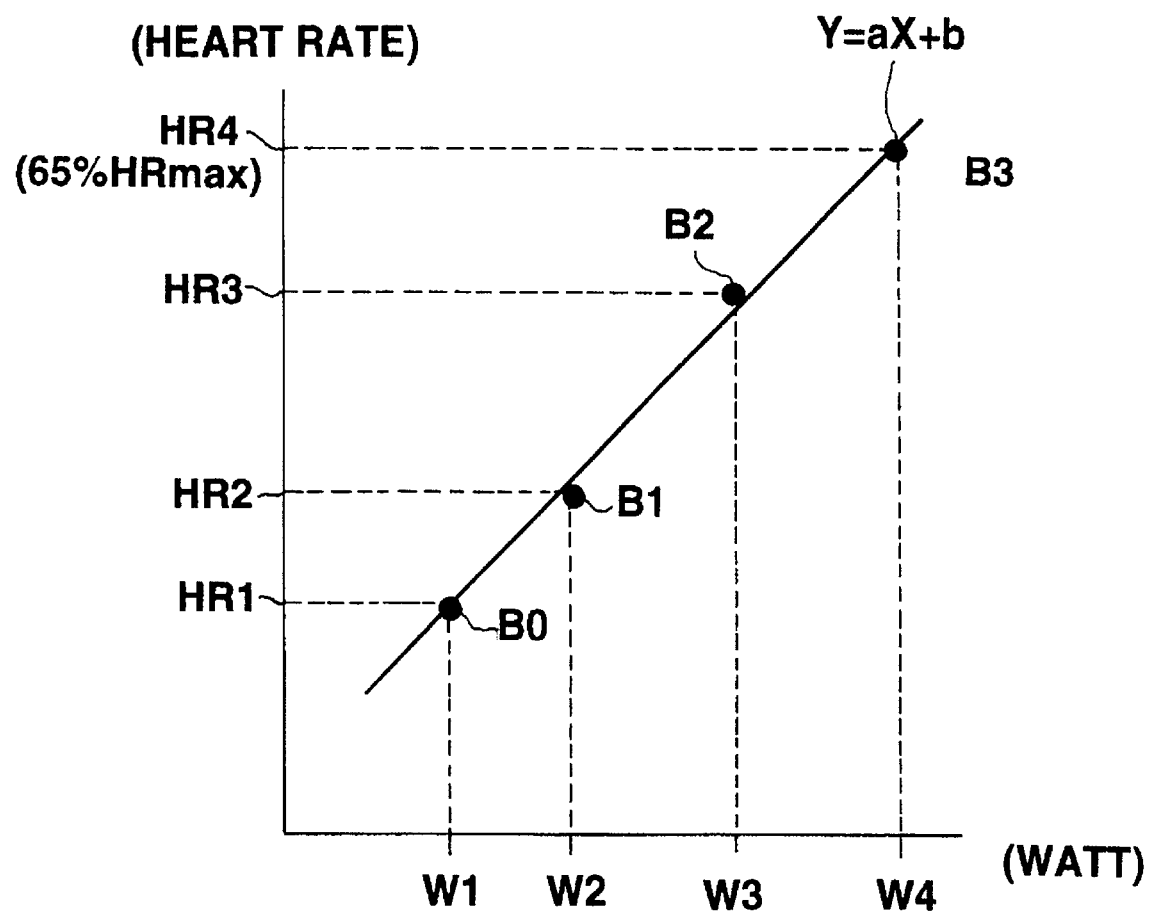
FIG. 7 is a graph showing relation between heart rates and work load.

FIG. 7 is a view showing a principle of calculating evaluation data for evaluating physical strength. In a graph of FIG. 7, the Y-distance represents number of pulses, i.e., heart rate and the X-distance represents work load W (watt). The work load W after the exerciser has taken the footstool up/down exercise three times at paces stored in the register S0, S1 and S2 will be calculated as follows:

W=[weight of an exerciser (Kg.)×9.8× a height of a footstool (m)× a pace/(4×60), where a coefficient 9.8 is the acceleration of gravity (m/s.s). The pace is represented in units of steps/minute. The footstool up/down exercise is a cyclic exercise of four steps, and, therefore, the number of cycles per second of the exercise is obtained by dividing the paces by 4×60.

In case work load of the first exercise is W1, and a heart rate which is measured after the exercise and stored in the register P1 is HR1, a point B0 is obtained in the graph of FIG. 7. Further, when work loads of the second and the third exercises are W2, W3, and heart rates are HR2, HR3, points B1 and B2 are obtained in the graph. From coordinate data of the points B0, B1 and B2, a regression expression Y=aX+b is obtained.

Then, a maximum heart rate HRmax for an age is calculated from the age. In general, it is said that the HRmax is calculated from an expression of "HRmax=220–age". But, in the present embodiment, the following expressions are used to calculate the maximum heart rates for male and female:

HRmax (male)=209–age×0.69 and

HRmax (female)=205–age×0.75

The above expressions are obtained from data of a number of exercisers.

Then, a heart rate (65% HRmax) corresponding to 65% of the calculated maximum heart rate HRmax is calculated. If the calculated HRmax is expressed by HR4 on the Y-distance of the graph of FIG. 7, substituting HR4 for Y in the equation Y=aX+b, a value X will be obtained. The value of X is work load of the exerciser at a heart rate of 65% HRmax.

The work load calculated in this way is stored in the register R, and, at the same time, is compared with a reference work load of the same age and the same sex stored in the ROM 2 to be evaluated in five-step levels. In other words, the calculated work amount is evaluated to judge whether it is in a fair level (a normal level), a good level, an excellent level, a poor level or an inferior level, compared with the reference work load of the same age and the same sex. The evaluation resultant is stored in the register R together with the work load.

After calculation of the evaluation data for evaluating physical strength at step A24, the operation goes to step A25, where the work load stored in the register R and the evaluation resultant expressed in the five step levels are displayed. In this case, the work load is displayed in terms of the calculated value, for example, "140 watt", and the evaluation resultant is shown by indications such as "FAIR", "GOOD", "EXCELLENT" and so on.

In the above embodiment, the measuring apparatus which is incorporated in the wrist watch has been described, but may be incorporated in other electronic devices. The measuring apparatus may be arranged to be specialized in evaluating physical strength.

Further, in the above embodiment, the exerciser performs footstool up/down exercise, but may perform other exercises such as a reciprocating step exercise of stepping aside to the left and to the right or may walk fast or jog a predetermined distance. The heart rate is measured to detect changes in data of a living body, which changes are caused by exercise, but oxygen intake or nitrogen dioxide excretion may be measured instead of the heart rate.

The exerciser performs the exercise at different paces to change exercise difficulty or exercise load, but footstools having different heights may be used for changing exercise load. Any ways which will substantially change exercise load may be employed.

In the above embodiment, the pulse sensor 8 incorporated in the wrist watch measures a heart rate, but a sensor mounted in a separate casing from the watch casing, for detecting an electrocardiowave may be used in place of the pulse sensor 8. The detecting sensor may be attached directly on a portion close to the heart of the exerciser under measurement, and data therefrom may be transferred to the wrist watch through a cable or by means of a radio wave.

With the use of the detecting sensor attached onto the body of the exerciser, measurement of the heart rate may be made even while the exerciser is performing the exercise, not after the exerciser has performed exercise.

Further, in the above embodiment, the evaluation of physical strength is made in the five step evaluation levels, but may be made in more than five step evaluation levels. The evaluation may be expressed in various ways such as in points or %.

Still further, in the above embodiment, the work load and the five step evaluation are displayed on the display device 5. But these work load and the five step evaluation may be printed out by a printer. It should be understood in the present specification, display of data includes that data are audibly output.

As described above, the measuring apparatus of the present invention is capable of absolutely evaluating physical strength of the user in terms of the five step evaluation levels. Therefore, the user can objectively evaluate his physical strength using the measuring apparatus to maintain or improve his physical strength.

What is claimed is:

1. A measuring apparatus comprising:

height setting means for setting a height of a footstool;

personal data setting means for setting personal data of an exerciser, the personal data including at least an age, weight and sex distinction;

pace-sound generating means for generating pace sounds for a footstool exercise, the pace sounds being generated plural times, each of the plural times providing a different exercise pace;

physical data measuring means for measuring physical data of the exerciser when the exerciser steps up on and down from the footstool, a height of the footstool being set by said height setting means, in synchronism with the pace sounds generated by said pace-sound generating means; and physical-strength evaluation data outputting means for calculating physical-strength evaluation data of the exerciser based on the physical data measured by said physical data measuring means, the height of the footstool set by said height setting means and the personal data set by said personal data setting means, and for outputting the calculated physical-strength evaluation data.

2. The measuring apparatus according to claim 1, further comprising:

display means for displaying the physical-strength evaluation data output by said physical-strength evaluation data outputting means.

3. The measuring apparatus according to claim 1, wherein the physical data to be measured by said physical data measuring means comprises a heart rate of the exerciser measured during a predetermined time.

4. The measuring apparatus according to claim 1, further comprising:

timer means for successively counting an exercise time during which the exerciser exercises and a rest time during which the exerciser rests after the exerciser finishes exercising and before the exerciser starts a next exercise, and wherein:
   said pace-sound generating means generates the pace sounds based on the exercise time counted by said timer means.

5. The measuring apparatus according to claim 1, further comprising:

a casing for containing said pace-sound generating means, said physical data measuring means and physical-strength evaluation data output means.

6. The measuring apparatus according to claim 1, wherein:

said pace-sound generating means generates the pace sounds to correspond to the age data included in the personal data of the exerciser set by said personal data setting means; and said physical data measuring means measures a heart rate of the exerciser when the exerciser steps up on and down from the footstool in synchronism with the pace sounds generated by said pace-sound generating means.

7. The measuring apparatus according to claim 1, wherein:

said physical-strength evaluation data outputting means includes display control means for displaying the physical-strength evaluation data calculated by said physical-strength evaluation data calculating means in terms of five step evaluation levels.

8. The measuring apparatus according to claim 1, wherein:

said physical-strength evaluation data outputting means calculates the physical-strength evaluation data that indicates whether a physical strength of the exerciser is one of superior, normal and poor compared with general physical strengths corresponding to the age data included in the personal data set by said personal data setting means.

* * * * *